(12) United States Patent
Lennon et al.

(10) Patent No.: US 8,889,102 B2
(45) Date of Patent: Nov. 18, 2014

(54) NEUROMYELITIS OPTICA AUTOANTIBODIES AS A MARKER FOR NEOPLASIA

(75) Inventors: Vanda A. Lennon, Rochester, MN (US); Sean J. Pittock, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 269 days.

(21) Appl. No.: 12/678,350

(22) PCT Filed: Sep. 19, 2008

(86) PCT No.: PCT/US2008/077005
§ 371 (c)(1),
(2), (4) Date: May 24, 2010

(87) PCT Pub. No.: WO2009/039363
PCT Pub. Date: Mar. 26, 2009

(65) Prior Publication Data
US 2010/0226860 A1 Sep. 9, 2010

Related U.S. Application Data

(60) Provisional application No. 60/974,019, filed on Sep. 20, 2007.

(51) Int. Cl.
*G01N 33/50* (2006.01)
*G01N 33/53* (2006.01)
*G01N 33/564* (2006.01)
*G01N 33/574* (2006.01)
*G01N 33/543* (2006.01)
*A61K 49/06* (2006.01)

(52) U.S. Cl.
CPC ........ *G01N 33/57488* (2013.01); *G01N 33/564* (2013.01); *G01N 2333/705* (2013.01)
USPC ............ 424/9.3; 436/514; 436/516; 436/517; 436/518; 436/547; 436/548; 436/543; 436/544; 436/545; 436/546; 424/9.1; 424/9.4; 424/9.6

(58) Field of Classification Search
None
See application file for complete search history.

(56) References Cited

U.S. PATENT DOCUMENTS 7,101,679 B2 9/2006 Lennon et al.

OTHER PUBLICATIONS

't Hart et al. Curr. Opin. Neurol. 2003. 16: 375-383.*
Earnest et al. Radiology. 1999. 211: 137-145.*
Pittock et al. Curr. Opin. Neurol. 2006, 19: 362-368.*
The fact sheet of paraneoplastic neurological disorder retrieved from the website "Paraneoplastic Neurological Disorders—Information for Patients: Overview of Paraneoplastic Neurological Disorders "www.penncancer.org/pnd/subpage.cfm?s=1&ss=2&ss=18 on Jun. 4, 2014.*
The wiki of Paraneoplastic syndrome, retrived from the wiki website on Jun. 4, 2014.*
Lennon et al. Lancet 2004; 364: 2106-12.*
GenBank Accession No. AAB26957, dated Nov. 22, 1996, 1 page.
GenBank Accession No. AAB26958, dated Nov. 22, 1996, 1 page.
GenBank Accession No. AAG17964, dated Oct. 3, 2000, 1 page.
GenBank Accession No. BC022286, dated Jul. 15, 2006, 2 pages.
GenBank Accession No. 139178, dated May 13, 1997, 1 page.
GenBank Accession No. NM_004028, dated Jan. 2, 2011, 4 pages.
GenBank Accession No. U63622, dated Nov. 22, 1996, 1 page.
GenBank Accession No. U63623, dated Nov. 22, 1996, 1 page.
GenBank Accession No. NM_001650, dated Jan. 2, 2011, 4 pages.
Neely et al., "Syntrophin-dependent expression and localization of Aquaporin-4 water channel protein," *PNAS*, 2001, 98:14108-14113.
Wingerchuk et al., "The spectrum of neuromyelitis optica," *The Lancet Neurology*, 2007, 6:805-815.
Lennon et al., "IgG marker of optic-spinal multiple sclerosis binds to the aquaporin-4 water channel," *J. Exp. Med.*, 2005, 202:473-477.
Authorized Officer Dorothée Mülhausen, International Preliminary Report on Patentability, PCT/US2008/077005.

* cited by examiner

*Primary Examiner* — Chang-Yu Wang
(74) *Attorney, Agent, or Firm* — Fish & Richardson P.C.

(57) ABSTRACT

The present invention provides for methods and materials for diagnosing and treating neuromyelitis optica (NMO).

5 Claims, 4 Drawing Sheets

```
AccI        GT'mk_AC  (0 Err) - 2 Fragment(s)
    243       909

ApaI        G_GGCC'C  (0 Err) - 2 Fragment(s)
    402       750

BamHI       G'GATC_C  (0 Err) - 2 Fragment(s)
    200       952

EcoRI       G'AATT_C  (0 Err) - 2 Fragment(s)
    343       809

HindIII     A'AGCT_T  (0 Err) - 2 Fragment(s)
    138       1017

NciI        CC's_GG   (0 Err) - 2 Fragment(s)
    196       966

NcoI        C'CATG_G  (0 Err) - 4 Fragment(s)
    40        135     288     669

PstI        C_TGCA'G  (0 Err) - 3 Fragment(s)
    337       366     449

PvuII       CAG'CTG   (0 Err) - 2 Fragment(s)
    578       683

SalI        G'TCGA_C  (0 Err) - 2 Fragment(s)
    242       910

== Linear Map of Sequence:

1   ggggtcaggcaatgagagctgcactctggctgggaaggcatgagtgacagcccacagca   60
          cccagtccgttactctcgacgtgagaccgacccttcgtactcactgtctgggtgtcgt 61   aggcggtggggtaagtgtggacctttgtgtaccagagagaacatcatggtggctttcaaa  120
          tccgccaccccattcacacctggaaacacatggtctctcttgtagtaccaccgaaagttt HindIII
                       \
    121   ggggtctggactcaagcttctggaaagcagtcacagcggaatttctggccatgcttatt   180
          cccagacctgagttcgaagaccttttcgtcagtgtcgcctttaaagaccggtacgaataa BamHI
                       \
    181   tttgttctcctcaagcctgggatccaccatcaactggggtggaacagaaaagccttaccg  240
          aaacaagaggagttcggaccctaggtggtagttgaccccaccttgtcttttcggaatggc SalI
```

FIG. 2-3

NEUROMYELITIS OPTICA AUTOANTIBODIES AS A MARKER FOR NEOPLASIA

CROSS-REFERENCE TO RELATED APPLICATIONS

This application is a National Stage application under 35 U.S.C. §371 and claims benefit under 35 U.S.C. §119(a) of International Application No. PCT/US2008/077005 having an International Filing Date of Sep. 19, 2008, which claims the benefit of priority of U.S. Application No. 60/974,019 having a filing date of Sep. 20, 2007.

TECHNICAL FIELD

This invention relates generally to neurological disorders, and more particularly, to an autoantibody marker for neuromyelitis optica (NMO) and its correlation with neoplasia.

BACKGROUND

Neuromyelitis optica (NMO) is a neurological disorder also known as Devic's syndrome in Western countries and as opticopinal multiple sclerosis in Asia. NMO has been regarded as a severe variant of multiple sclerosis (MS), and the antigen was recently identified as aquaporin-4.

SUMMARY

This disclosure describes a correlation between the presence of NMO and the NMO antigen, aquaporin-4, and neoplasia.

In one aspect, the invention provides for methods of detecting neoplasia in an individual presenting with a neurological disorder. Such methods generally include providing a biological sample from the individual presenting with neurological symptoms; determining whether or not aquaporin-4-specific autoantibodies are present in the biological sample; and screening said individual for neoplasia if said aquaporin-4-specific autoantibodies are present in said biological sample.

Representative biological samples include blood, serum, plasma, cerebrospinal fluid, and tissue biopsy. In some embodiments, the determining step is by immunoassay, and the screening step is by MRI or immunoassay. Representative neoplasias include, without limitation, breast cancer, bladder cancer, lymphoma, thyroid cancer, thymic cancer, cervical cancer, lung cancer, lung adenocarcinoma, and thymoma. Representative neurological symptoms include vision impairment, tingling, numbness, weakness, limb spasms, and loss of bladder and/or bowel control.

In another aspect, the invention provides methods of diagnosing an individual with neoplasia. Such methods generally include identifying an individual having neurological symptoms; and screening the individual for neoplasia. Representative neurological symptoms include vision impairment, tingling, numbness, weakness, limb spasms, and loss of bladder and/or bowel control.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods and examples are illustrative only and not intended to be limiting. All publications, patent applications, patents and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 2 is a restriction map of a human aquaporin-4 nucleic acid.

Like reference symbols in the various drawings indicate like elements.

DETAILED DESCRIPTION

Figure 1:
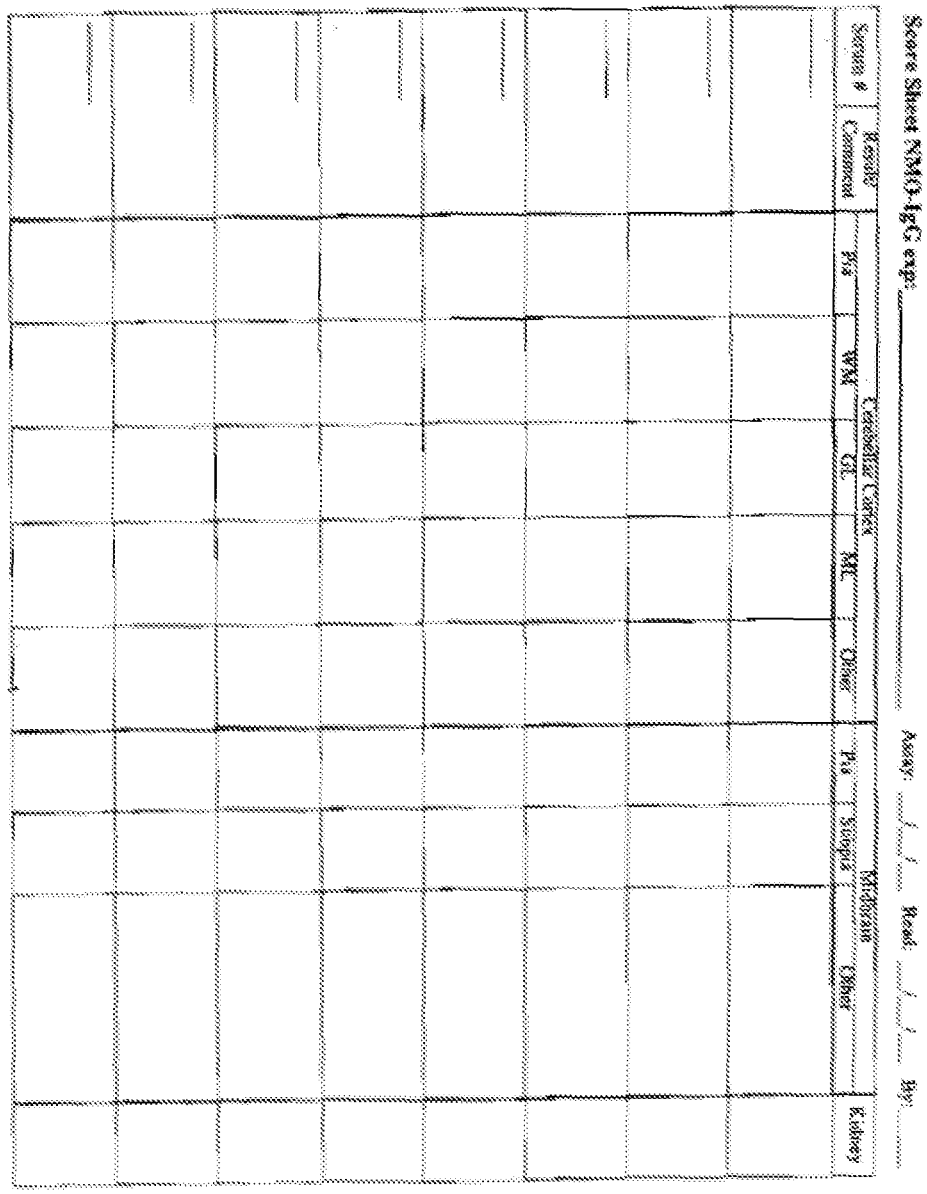
FIG. 1 is a score sheet used to evaluate the immunohistochemical staining pattern and intensity of tissues contacted with serum from an individual.

This disclosure describes a correlation between the presence of neurological symptoms and neoplasia. In some, but not all, cases, the neurological symptoms have been associated with NMO, an autoimmune disease. The NMO antigen was recently described in U.S. Pat. No. 7,101,679 (incorporated herein by reference) as aquaporin-4. Based on the present disclosure, individuals that exhibit or have exhibited neurological symptoms can be screened for a neoplasia.

Neurological symptoms include, but are not limited to, vision impairment and/or tingling, numbness, weakness, limb spasms, loss of bladder and/or bowel control, or other neurological symptoms of unknown origin. Neoplasias include, but are not limited to, breast cancer, bladder cancer, lymphoma, thyroid cancer, thymic cancer, pancreatic cancer, cervical cancer, brain cancer (e.g., glioblastoma), lung cancer or adenocarcinoma, thymoma, prostate cancer, colorectal cancer, renal cancer, adrenal cancer, liver cancer, neurofibromatosis 1, and leukemia. A neoplasm can be a solid neoplasm (e.g. sarcoma or carcinoma) or a cancerous growth affecting the hematopoietic system (e.g., lymphoma or leukemia). Methods of detecting neoplasia or screening an individual for neoplasia are well known in the art and include, for example, blood or sera tests (e.g., immunoassays), MRI and/or CAT scans, and/or tissue biopsies.

If so desired, the presence or absence of an aquaporin-4 autoantibody (i.e., a NMO-specific autoantibody) can be determined prior to or after screening the individual for neoplasia. The methods of the invention are based on an association between the presence of abnormal neurological symptoms in an individual, oftentimes manifested in NMO (i.e., NMO-specific autoantibodies), and the presence of neoplasia. The present invention provides for methods of detecting neoplasia in an individual exhibiting neurological symptoms.

If so desired, the methods and compositions disclosed in U.S. Pat. No. 7,101,679 can be used to detect the aquaporin-4 autoantibody in an individual. Briefly, an aquaporin-4 polypeptide or an antigenic fragment thereof can be used to detect the presence or absence of the aquaporin-4 autoantibody in a biological sample using any of a number of immunological techniques. Aquaporin-4 polypeptides, antigenic fragments thereof, and methods of detecting an aquaporin-4 autoantibody are disclosed in U.S. Pat. No. 7,101,679. A representative antigenic fragment can include, for example, the extracellular domain of a membrane-bound protein.

Depending on the nature of the biological sample, immunological techniques include either or both immunoassays (e.g., enzyme-linked immunosorbent assays (ELISA), Western blot, and radioimmunoassay) and immunocytochemical staining techniques. Both types of immunological techniques are used routinely in the art and can be used to detect the presence of aquaporin-4-specific autoantibodies in a biological sample. A "biological sample," as used herein, is generally a sample from an individual. Non-limiting examples of biological samples include blood, serum, plasma, or cerebrospinal fluid. Additionally, solid tissues, for example, spinal cord or brain biopsies may be used.

The term "aquaporin-4" refers to a member of the aquaporin family. The aquaporin family has 10 known members. Aquaporin-4 is expressed in the astrocytic foot process membrane contacting capillaries in the central nervous system, and also in the basolateral membrane of renal distal collecting tubules. Examples of a nucleotide sequence encoding a human aquaporin-4 polypeptide are shown in GenBank Accession Nos. U63622 and U63623. The predicted amino acid sequences of representative human aquaporin-4 polypeptides are shown in GenBank Accession Nos. AAG17964, AAB26957, AAB26958, and I39178. Nucleic acid and amino acid sequences encoding aquaporin-4 from other organisms (e.g., *Mus musculus, Bos Taurus, Rattus norvegicus*, and *Ovis aries*) can be found by searching the GenBank database (at ncbi.nlm.nih.gov on the World Wide Web) using "aquaporin-4" as the search word.

Aquaporin-4 antigenic polypeptides can be obtained using standard methods (for example, from cells (e.g., transfected host cells) expressing a nucleic acid or synthetically-generated) and can be purified, defined as a polypeptide that constitutes the major component in a mixture of components, e.g., 50% or more, 60% or more, 70% or more, 80% or more, 90% or more, or 95% or more, by weight, using routine protein purification methods, including affinity chromatography or immunosorbant affinity column. Aquaporin-4 antigenic polypeptides and methods of making and identifying such antigenic polypeptides are described fully in U.S. Pat. No. 7,101,679.

As used herein, nucleic acid refers to RNA or DNA. With respect to nucleic acids, "isolated" refers to (i) a nucleic acid sequence encoding part or all of the human aquaporin-4 polypeptide, but free of coding sequences that normally flank one or both sides of the nucleic acid sequences encoding aquaporin-4 in the human genome; or (ii) a nucleic acid incorporated into a vector or into the genomic DNA of an organism such that the resulting molecule is not identical to any naturally-occurring vector or genomic DNA.

Fragments of the human aquaporin-4 nucleic acid and polypeptide also are provided. As used herein, fragments refer to nucleic acids or polypeptides corresponding to less than the entire aquaporin-4 sequence. Such fragments may, for example, encode an aquaporin-4 antigenic polypeptide fragment, or have utility as hybridization probes or amplification primers. FIG. 2 shows the relative position of various restriction enzyme sites within a human aquaporin-4 nucleic acid sequence that, by way of example, define positions, which, in various combinations, can be used to generate useful nucleic acid fragments. Given the nucleotide sequence of a human aquaporin-4 polypeptide, virtually any nucleic acid fragment can be generated by known means (e.g., restriction enzyme digestion, the polymerase chain reaction) and, if so desired, expressed to produce the corresponding polypeptide fragment. Alternatively, the human aquaporin-4 polypeptide can be cleaved (e.g., proteolytically) to directly generate polypeptide fragments.

An aquaporin-4 nucleic acid or nucleic acid fragment may have a sequence that deviates from that shown, for example, in GenBank Accession Nos. U63622 or U63623. For example, a nucleic acid sequence can have at least 80% sequence identity, at least 85% sequence identity, at least 90% sequence identity, at least 95% sequence identity, or at least 99% sequence identity to GenBank Accession Nos. U63622 and U63623. See, for example, GenBank Accession Nos. BC022286, NM_004028, and NM_001650 for variant nucleic acid sequences of aquaporin-4. Percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. The total number of aligned nucleotides or amino acids refers to the minimum number of aquaporin-4 nucleotides or amino acids that are necessary to align the second sequence, and does not include alignment (e.g., forced alignment) with non-aquaporin-4 sequences, such as those fused to aquaporin-4. The total number of aligned nucleotides or amino acids may correspond to the entire aquaporin-4 sequence or may correspond to fragments of the full-length aquaporin-4 sequence as defined herein.

Sequences can be aligned using the using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web. BLAST searches or alignments can be performed to determine percent sequence identity between an aquaporin-4 nucleic acid molecule and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an aquaporin-4 sequence and another sequence, the default parameters of the respective programs are used.

A nucleic acid encoding an aquaporin-4 polypeptide may be obtained from, for example, a cDNA library made from a human cell line, or can be obtained by other means, including, but not limited to, the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach & Dveksler, Eds., Cold Spring Harbor Laboratory Press, 1995. Generally, sequence information from the ends of the region of interest or beyond is employed to design oligonucleotide primers that are identical or similar in sequence to opposite strands of the template to be amplified. In addition, aquaporin-4 nucleic acids can be detected by, for example, a variety of hybridization techniques. Hybridization between nucleic acid molecules is discussed in detail in Sambrook et al. (1989, *Molecular Cloning: A Laboratory Manual*, 2$^{nd}$ Ed., Cold Spring Harbor Laboratory Press, Cold Spring Harbor, N.Y.; Sections 7.37-7.57, 9.47-9.57, 11.7-11.8, and 11.45-11.57).

The present invention further includes vectors containing an aquaporin-4 nucleic acid or the complement thereof, an aquaporin-4 nucleic acid fragment or the complement thereof, and those nucleic acids having at least 80% sequence identity to an aquaporin-4 nucleic acid or fragments generated therefrom (or the complements thereof). Cloning vectors suitable for use in the present invention are commercially available and used routinely by those of ordinary skill. Vectors of the invention may additionally comprise elements necessary for expression operably linked to a human aquaporin-4 nucleic acid sequence. "Elements necessary for expression" include promoter sequences, and additionally may include regulatory elements, such as enhancer sequences, response elements or inducible elements that modulate expression of the human aquaporin-4 nucleic acid sequence. As used herein, "operably linked" refers to positioning of a promoter and/or other regulatory element(s) in a construct relative to the human aquaporin-4 nucleic acid sequences in such a way as to direct or regulate expression of the aquaporin-4 nucleic acid.

As used herein, the term "host" or "host cell" is meant to include not only prokaryotes, such as *E. coli*, but also eukaryotes, such as yeast, insect, plant and animal cells. Animal cells include, for example, COS cells and HeLa cells. A host cell can be transformed or transfected with a DNA molecule (e.g., a vector) using any of the techniques commonly known to those of ordinary skill in this art, such as calcium phosphate or lithium acetate precipitation, electroporation, lipofection and particle bombardment. Host cells containing a vector of the present invention may be used for purposes such as propagating the vector, producing aquaporin-4 nucleic acid (e.g., DNA, RNA, antisense RNA), or expressing an aquaporin-4 polypeptide or fragments thereof.

Methods of producing aquaporin-4 polypeptides also are provided and include, but are not limited to, culturing host cells containing an aquaporin-4 expression vector under conditions permissive for expression of aquaporin-4, and recovering the aquaporin-4 polypeptides. Methods of culturing bacteria and recovering expressed polypeptides are well known to those of ordinary skill in this art.

The invention will be further described in the following examples, which do not limit the scope of the invention described in the claims.

EXAMPLES

Example 1

Serum Preabsorption

To minimize non-specific staining, each patient's serum was preabsorbed with liver antigens by mixing 40 mg of commercial guinea pig tissue powder (Sigma Chemical Co., St. Louis, Mo.) with 10 μL of serum diluted in 590 μL of phosphate-buffered saline (PBS) containing 1% bovine serum albumen. After gently mixing for 1 hour at room temperature, insoluble residue was removed by centrifuging (20,800×g for 10 minutes). Fresh liver powder (40 mg) was then immediately added to the serum supernatant, and the process was repeated an additional two times for a total of 3 consecutive absorptions.

Example 2

Substrate Preparation

A frozen composite block of three normal mammalian tissues (e.g., mouse brain (both cerebellum and midbrain), stomach and kidney) was cryosectioned (4μ thickness) onto individual wells of an 8-well microscope slide. These slides were purchased as a custom product (from MeDiCa, Encinitas, Calif.) and stored at −70° C. in individual sealed packets containing desiccant. Before opening for use, each packet was equilibrated at room temperature. Chilled detergent (1% CHAPS in PBS) was applied to each section and aspirated after 4 minutes. After 3 washes in chilled PBS (each wash was for 5 minutes on a shaker), chilled 10% phosphate-buffered formalin was applied and aspirated after 4 minutes. After 3 more 5-minute washes in chilled PBS, PBS containing 10% normal goat serum (at room temperature) was applied and aspirated after 60 minutes.

Example 3

Immunostaining

Absorbed, diluted patient and control sera (40 μL volumes) were applied individually to wells containing the above-described treated tissue sections. After 40 minutes at room temperature, each well was washed thoroughly with chilled PBS. A commercial fluorochrome-conjugated IgG specific for human IgG (e.g., fluoresceinated goat anti-human IgG, Southern Biotechnology Assoc., Inc., Birmingham, Ala.) is then applied at the appropriate dilution. After 35 minutes at room temperature, the wells were washed thoroughly in chilled PBS and a glass coverslip (#1 thickness) was applied to each slide with mounting medium containing an anti-fade reagent. The slides were evaluated by fluorescence microscopy (20× objective) for the characteristic NMO pattern of tissue-bound IgG.

In the central nervous system (CNS), the NMO antigen was localized on the abluminal face of capillaries in the cerebellar cortex, midbrain and spinal cord; in optic nerve, the NMO antigen was associated with pia and astrocytic processes in the region of capillaries amongst axon columns. In optimally treated sections of CNS tissues, immunofluorescence confocal microscopy suggested that the NMO antigen is a component of the blood-brain barrier. Immunoreactivity was inherent in the glia limitans of the astrocytic-pial junction, extending into the Virchow-Robin space to the smallest capillaries in white matter and gray matter. Dual immunostaining with affinity-purified antibodies of defined specificity revealed co-localization of the NMO antigen with aquaporin-4, a mercurial-insensitive water channel protein constituent of the blood-brain-barrier. The NMO antigen is not detectable in sections of spleen or liver parenchyma but, like aquaporin-4, it is prominently associated with basolateral membranes of distal collecting tubules in the kidney, and with basal elements of deep gastric mucosal epithelium.

By using a limiting dilution of NMO-IgG in a competitive inhibition immunofluorescence assay, enrichment of immunoreactivity was demonstrated in the crude membrane fraction prepared from homogenized rat brain by differential centrifugation. This fraction potently quenched the NMO-IgG immunofluorescence pattern. Fractions containing tissue debris and nuclei were relatively depleted of immunoreactivity, and cytosol did not absorb the reactivity of NMO-IgG. The crude membrane fraction's immunoreactivity resisted extraction in a 2% solution of the non-ionic detergent CHAPS. This observation led to the discovery that treatment of tissue sections with 1% CHAPS for 4 minutes, before or after fixation for 4 minutes in 10% phosphate buffered formalin, preserved tissue morphology and enhanced the accessibility of NMO epitopes to IgG in serum of 70% of patients with a clinical diagnosis of NMO.

Although not bound by any particular theory, the resistance of the NMO antigen to detergent extraction is consistent with the proposed tethering of the cytoplasmic C-terminus of aquaporin-4 to a PDZ-domain of the scaffolding adapter protein α-syntrophin, which is a component of the dystrophin protein complex (Neely et al., *PNAS* 98:14108, 2001).

Example 4

Interpreting Immunohistochemical Staining Results

Table 1 shows the characteristic features that were evaluated in each of the indicated tissues:

TABLE 1

| | |
|---|---|
| cerebellum | pia, white matter matrix and capillaries, granular layer capillaries, and molecular layer capillaries |
| midbrain | pia, subpia, white matter and capillaries |
| kidney | distal collecting tubules (binds NMO-IgG most avidly) |
| stomach | basal epithelium of deep mucosa (binds NMO-IgG least avidly) |

The staining intensity of each characteristic is graded on a formal score sheet (FIG. 1), using the following scoring system:
negative: − or ±/−
faint positive, may be equivocal: ±
definite positive, strong: ±/+, + or 2+
A positive result requires a minimum of a '±' score to be assigned to the kidney's distal collecting tubules and to cerebellar or midbrain pia or capillaries.

The presence and intensity of any nuclear, cytoplasmic, membranous or extracellular matrix staining that may potentially interfere with NMO-IgG interpretation is noted. In particular, staining in any of the tissues indicated in Table 2 is noted for each tissue section examined.

TABLE 2

| | |
|---|---|
| cerebellum/midbrain | neurons, myelin, arteriolar smooth muscle |
| stomach | mucosal epithelium, enteric neurons, and smooth muscle |
| kidney | cortical tubules, glomeruli, arterioles, sympathetic nerves, other |

Example 5

Clinical Application

Serum was analyzed from patients classified as "definite" NMO, the Asian opticospinal form of MS, or classical MS by clinical, imaging and spinal fluid criteria, and from control patients, for autoantibodies that might bind selectively to CNS tissues. The experiments described herein demonstrate the value of seropositivity for discriminating NMO from the classic form of multiple sclerosis (MS). Sera (coded at testing) were from patients with definite NMO using diagnostic criteria of varying grades of stringency (n=45), patients with classic MS (n=19), patients deemed to be at high risk for MNO (bilateral optic neuritis or single or recurrent attacks of longitudinally extensive myelitis; each associated with negative brain MRI, i.e., not fulfilling stringent criteria for "definite" NMO classification) (n=35), and patients ultimately diagnosed with MS but initially presenting with optic neuritis or myelitis (n=22). Indirect immunofluorescence was performed with a standard composite substrate of mouse brain, gut and kidney; sera were preabsorbed with liver extract as described above in Example 1.

IgG in 33 of 45 patients (73%) with NMO yielded a distinctive staining pattern ("NMO-IgG") associated with capillaries throughout the cerebellar cortex and midbrain, and with pia and a subpial "mesh" (prominent in midbrain). The capillary pattern was not seen in gut mucosa, kidney, or liver, and NMO-IgG was not noted in any control disease group. Sera from 16 out of 35 patients (46%) that were at high risk for NMO yielded the staining pattern distinctive for NMO-IgG. None of the 19 patients diagnosed with classic MS had detectable staining patterns of NMO-IgG, while sera from 2 out of the 22 patients (9%) that presented with optic neuritis/myelitis possessed the NMO-IgG.

Additionally, a NMO-IgG was identified incidentally in 14 patients amongst 85 thousand whose sera were submitted to Mayo Clinic's Neuroimmunology Laboratory for blinded paraneoplastic autoantibody testing on a service basis. Their subsequently-obtained histories revealed that 3 fulfilled clinical criteria for the diagnosis of NMO, 9 were classified as high risk for NMO (7 had longitudinally extensive myelitis and 2 had recurrent optic neuritis), 1 had new onset myelopathy, and 1 had unclassified steroid-responsive CNS inflammatory disorder.

These results indicated that the NMO-IgG autoantibody is the first specific biological marker of NMO and is able to distinguish NMO from MS.

Example 6

Western Blot

A GST fusion protein containing recombinant rat aquaporin-4 (C terminal residues 249-323; Alamone Labs, Jerusalem, Israel) was electrophoresed in a 10% polyacrylamide gel in standard Laemmli SDS buffer containing β-mercaptoethanol, and a Western blot was performed using NMO patients' and immune rabbit's serum as a positive control to determine whether or not the patients' IgG would bind to the 38 kDa GST-aquaporin-4 fusion protein. The blot was contacted with human sera (1:50 dilution), which included 4 NMO patients, 3 normal persons, 1 control myelopathy, 2 patients with classic MS, and 3 patients with miscellaneous neuropsychiatric disorders. Serum from the four NMO patients and from the immune rabbit, but none of the serum from the control patients or from patients exhibiting the other disorders, bound the 38 kDa aquaporin-4 fusion protein.

Example 7

Methods Used to Validate NMO Autoantibodies as a Tumor Biomarker

The Mayo Clinic Neuroimmunology Laboratory identified 14 patients with NMO-IgG in the context of cancer in one of two ways (Table 1):

1) 7 patients incidentally in the course of prospective indirect immunofluorescence testing on a service basis for paraneoplastic autoantibodies. Neurological findings in 5 were consistent with an NMO spectrum disorder.

2) 7 patients with AQP4-specific-IgG detected in the course of service NMO-IgG testing by laboratory-based physician review of available clinical correlative notes for quality assurance purposes. Neurological findings in all 7 were consistent with an NMO spectrum disorder.

Each serum was titrated in doubling dilutions to ascertain by immunofluorescence (as described in Wingerchuk et al., 2007, The Lancet Neurology, 6:805-815) the farthest dilution that was positive. When serum was sufficient (n=8), immunoprecipitation assay was performed using GFP-AQP4 solubilized from stably transfected HEK 293 cells as antigen and protein G-agarose as immunoprecipitant (as described in Lennon et al., 2005, J. Exp. Med., 202:473-477).

Six patients were evaluated clinically at the Mayo Clinic. Information for the other 8 patients was obtained by physician telephone interview, form letters and review of case records provided by outside physicians. The study was approved by the Mayo Clinic Institutional Review Board (IRB 1559-03).

Example 8

Results Demonstrating that NMO Autoantibodies are a Tumor Biomarker

Table 3 summarizes the neurological presentations and cancers identified for the 14 NMO-IgG seropositive patients of this report. Thirteen (93%) were female and 7 (50%) had African ethnicity. Three patients of the 6 evaluated at the Mayo Clinic (50%) were African American. Less than 10% of contemporaneous patients registered in Mayo Clinic's Neurology Department had African ethnicity.

Twelve patients (86%) had neurological symptoms and signs fitting the currently recognized spectrum of NMO: 7 fulfilled diagnostic criteria for NMO (as described in Wingerchuk et al., 2007, *The Lancet Neurology*, 6:805-815), 3 had recurrent/relapsing LETM, and 2 had a single episode of LETM. The median age at onset of neurological symptoms was 50 (range 18-70), and in 5 patients, the NMO/LETM began within 6 months of the cancer diagnosis. In 3 patients, the NMO/LETM onset preceded the diagnosis of cancer by a median of 3 months (range 3-60). In 9 patients, the diagnosis of cancer preceded the NMO/LETM onset by a median of 12 months (range 3-120). The other 2 patients (Nos. 5 and 13 in Table 3) had lung and breast carcinomas but lacked symptoms or signs referable to the optic nerves or spinal cord. Their neurological symptoms and signs were attributable to brain metastases (MRI compatible in both and spinal fluid cytology positive in patient 13).

The most recent neoplasms identified in these 14 patients were: 5 breast carcinomas, 2 lung carcinomas, 2 thymic epithelial neoplasms (1 thymoma, 1 invasive carcinoma), and 1 each of thyroid (Hürthle cell) carcinoma, uterine cervical carcinoma, carcinoid, B-cell lymphoma (plasmacytoid small-cell) and pituitary somatropinoma.

These results justify consideration of underlying neoplasm in patients presenting with transverse myelitis or optic neuritis. In addition, since breast carcinoma accounted for 5 of the neoplasms identified among the 14 patients and since there is a 9-fold higher prevalence of NMO in females, women presenting with an NMO spectrum disorder should be examined for occult breast carcinoma. The detection of NMO-IgG in two patients whose neurological symptoms were attributable to CNS metastases of breast and lung carcinomas increases the likelihood that neoplastic cells were the source of antigen initiating the AQP4 immune response in all 14 patients described herein.

TABLE 3

Neurological presentations and cancers found in 14 NMO-IgG-positive patients.

| | Sex/ ethnicity | NMO-IgG titer | Neurological Diagnosis | Years of age at diagnosis of neurological disorder | Most recent neoplasm | Months between cancer and NMO or LETM diagnosis$^\Psi$ |
|---|---|---|---|---|---|---|
| 1 | M/C | 15,360* | rLETM | 70 | Seminoma (met), bladder carcinoma, lymphoma | −288, −140, −18 |
| 2 | F/Af/Ar | 1920* | NMO | 36 | Breast carcinoma (met) | 5 |
| 3 | F/C | 120 | NMO | 53 | Thyroid (Hurthle cell) | −12 |
| 4 | F/Af | 7680* | NMO | 44 | Thymic carcinoma | −3 |
| 5 | F/C | 7,680* | Cerebral metastasis | 63† | Lung carcinoma | NA |
| 6 | F/Af | 15,360* | rLETM | 18 | Cervical carcinoma | 3 |
| 7 | F/Af | 7,680 | rLETM | 49 | Breast carcinoma | −6 |
| 8 | F/Af | 30,720* | LETM | 66 | Lung adenocarcinoma | Anteceded LETM; (interval unknown) |
| 9 | F/C | 480 | NMO | 51 | Carcinoid | −96 |
| 10 | F/C | 120 | NMO | 55 | Breast carcinoma | 60 |
| 11 | F/Arg | 1,920 | NMO | 31 | Pituitary somatotropinoma | −3 |
| 12 | F/C | 15,360 | LETM | 63 | Breast carcinoma (infiltrating ductal) | −14 |

TABLE 3-continued

Neurological presentations and cancers found in 14 NMO-IgG-positive patients.

| | Sex/ethnicity | NMO-IgG titer | Neurological Diagnosis | Years of age at diagnosis of neurological disorder | Most recent neoplasm | Months between cancer and NMO or LETM diagnosis$^\Psi$ |
|---|---|---|---|---|---|---|
| 13 | F/Af | 1920* | Cerebral metastasis | 55† | Breast carcinoma | NA |
| 14 | F/Af | 7680 | NMO | 37 | Thymoma¥ | −120 |

Abbreviations:
Af, african;
Ar, arabic;
Arg, argentinian;
C, caucasian;
F, female;
M, male;
NMO, neuromyelitis optica;
LETM, longitudinally extensive myelitis;
r, recurrent;
*Indicates NMO-IgG detected incidentally in the immunofluorescence screening component of service paraneoplastic evaluation;
†patients lacked evidence of NMO/LETM; #13 had headache and diplopia due to hydrocephalus; symptoms resolved following ventriculo-peritoneal shunt;
¥Myasthenia gravis anteceded NMO by 10 years;
$\Psi$negative sign indicates cancer diagnosed first.
NA = not applicable

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting neoplasia in an individual presenting with a neurological disorder selected from the group consisting of neuromyelitis optica (NMO) or longitudinally extensive transverse myelitis (LETM), comprising: providing a biological sample from said individual presenting with neurological symptoms associated with said neurological disorder; determining that aquaporin-4-specific autoantibodies are present in said biological sample using an immunoassay; and screening said individual for neoplasia using MRI; wherein said neoplasia is bladder cancer, thyroid cancer, cervical cancer and lung adenocarcinoma.

2. The method of claim 1, wherein said biological sample is selected from the group consisting of blood, serum, plasma, cerebrospinal fluid, and tissue biopsy.

3. The method of claim 1, wherein said neurological symptoms are selected from the group consisting of vision impairment, tingling, numbness, weakness, limb spasms, and loss of bladder and/or bowel control.

4. The method of claim 1, wherein the immunoassay is selected from the group consisting of immunoassays and immunocytochemical staining.

5. The method of claim 4, wherein the immunoassays are selected from the group consisting of enzyme-linked immunosorbent assays (ELISA), Western blots, and radioimmunoassays.

* * * * *